United States Patent [19]

Myers et al.

[11] 4,436,949
[45] Mar. 13, 1984

[54] OLEFIN CONVERSION PROCESS

[75] Inventors: John W. Myers; Daniel J. Strope, both of Bartlesville, Okla.

[73] Assignee: Phillips Petroleum Company, Bartlesville, Okla.

[21] Appl. No.: 420,970

[22] Filed: Sep. 21, 1982

[51] Int. Cl.³ ........................... C07C 5/24; C07C 5/30
[52] U.S. Cl. .................................. 585/664; 585/643; 585/644; 585/671
[58] Field of Search ............... 585/643, 644, 664, 665, 585/666, 667, 668, 669, 670, 671

[56] References Cited

U.S. PATENT DOCUMENTS 3,558,734  1/1971  Myers .................................. 585/664
4,367,362  1/1983  Franz et al. ......................... 585/664

FOREIGN PATENT DOCUMENTS 2484400  12/1981  France ............................... 585/664

OTHER PUBLICATIONS

Tung et al., J. of Catalysis, vol. 3, 229–238, (1964).

*Primary Examiner*—Delbert E. Gantz
*Assistant Examiner*—A. Pal

[57] ABSTRACT

A novel process for the conversion of olefins is provided by adding water to said olefin and thereafter contacting said olefin with an acidic alumina catalyst under conditions sufficient to effect the conversion of said olefin.

19 Claims, No Drawings

OLEFIN CONVERSION PROCESS

This invention relates to the conversion of olefins.

As used herein, the term "olefin conversion" includes olefin disproportionation reactions. It can also include the process of olefin isomerization.

The conversion of olefins in the presence of an alumina catalyst is known in the art as disclosed in U.S. Pat. No. 3,395,196. However, processes which allow for greater olefin conversion than has been achieved in the art wherein an alumina catalyst has been used are highly desirable. This is because certain olefinic conversion products can have important commercial and industrial applications. For example, isobutene which is achieved from the disproportionation of propylene and isomerization of n-butene can be reacted with methanol to form methyl tertiary butyl ether (MTBE) which is useful as an additive in gasoline as an octane improver.

Therefore, an object of this invention is to provide an improved process for the conversion of olefins.

Other aspects, objects, and the several advantages of the present invention are apparent from this disclosure and the claims.

In accordance with the present invention, we have discovered that by adding water in an amount of at least 0.10 mole percent to at least one olefin and thereafter contacting the resulting wet olefin with an acidic alumina catalyst under conditions sufficient to effect conversion of such olefin that improved conversion of said olefin will occur.

Olefins contemplated for use in the present invention are ones containing from 3 to 16 carbon atoms. Such olefins include but are not limited to ethylene, propylene, butene, pentene, octene, and dodecene.

In a preferred embodiment, the mole percent of water added to the olefin feed will be from about 0.3 to about 100% of the hydrocarbon feed and more preferably from 0.3 to 50%. The water can be added to the olefin feed as a liquid, as steam, or can be introduced as oxygen or air-the water being formed in situ within the reaction zone, through the oxidation of hydrogen to form water.

The acidic alumina catalysts utilized in the present invention are those known in the art. Preferably, the alumina should have a surface area of at least 50 m$^2$/g. In the practice of the present invention, the alumina is used without the incorporation of substantial amounts of inert solids and does not contain substantial amounts of impurities. Good results are obtained with aluminas having a purity of at least about 99.50 weight percent. The alumina can be in any desired form suitable for contact with the olefin including for example granules, spheres, microspheres, pellets, tablets, fluid powder, etc. Preferable alumina catalysts include catalytic eta-alumina and gamma-alumina.

The catalyst can be employed in any manner conventional within the art, such as in a fixed bed, a fluidized bed and the like.

The conversion process can be carried out either batch-wise or continuously, using a fixed catalyst bed, stirred batch reactor, a fluidized catalyst chamber, or other suitable contacting techniques. The process conditions should be suitable to carry out the conversion of the particular olefin involved.

In general, the process can be carried out at a temperature from 600° to 1200° F., preferably from about 850° F. to about 1000° F. Any convenient pressure can be used, with the lowest practical pressure preferred in order to minimize side reactions such as polymerization. Pressures ranging from atmospheric to 200 psig are particularly suitable.

The LHSV is generally in the range of about 0.1 to 30 volume liquid olefin/volume of catalyst/hr., preferably about 0.2-20.

Generally, the reaction time will be in the range from about 0.5 hours to about 24 hours.

In the process of the present invention, butene can be converted by disproportionation to propylene and pentenes (i.e. normal and iso-) as shown in Example IV which follows.

In addition, propylene may be converted by disproportionation to ethylene and normal butene according to the process of this invention. In the same process, n-butene (either n-1-butene or n-2-butene) is isomerized to isobutene.

The following examples further illustrate the invention.

EXAMPLE 1

In this example, the olefin conversion of n-butene on an acidic alumina catalyst is described. The butene feed was a pure grade 2-butene of Phillips Petroleum Company, Bartlesville. The alumina catalyst was Catapal alumina (BET surface area: 219 m$^2$/g; sodium content, 0.003 weight %), marketed by Conoco, Inc. The alumina powder was extruded and pelletized into pellets having a diameter of approximately 1/16" by Harshaw Chemical Company, a unit of Gulf Oil Corporation, Cleveland, Ohio. Alumina was dried at 350° C. for 4 hours under nitrogen.

Isomerization runs were carried out in a quartz tube reactor of 0.79 inch outer diameter and 22 inches overall length. The reactor was loaded in descending order with a ¼ inch quartz wool plug, 6½ inches of quartz chips, another ¼ inch quartz wool plug, 4½ inches of Al$_2$O$_3$ catalyst (25 cc), and a final ¼ inch quartz wool plug. The reactor was fitted with an axial ¼-inch thermocouple well and was heated in a 16 inch, 3-zone furnace.

Process temperatures were varied between 890° F. and 950° F. at essentially atmospheric pressure (0 psig). The catalyst was generally regenerated by passing a mixture of 84 standard liters/hr of N$_2$ and 8.4 standard liters/hr of air through the reactor at temperatures ranging from 890° F. to 975° F. Regeneration cycles usually lasted from about 1-4 hours.

n-Butene feed gas was passed through a regulator, a drier tube containing 3A molecular sieve desiccant, a rotameter, and a fritted disc water saturator (when water was added with the feed) before entering the reactor. Additional water, if needed, was fed by a syringe pump to the top of the reactor. Regeneration gas was passed through a 500 mL saturator to saturate, if needed, the gas to a level of about 2.5-3.0 mole percent water. A gas sammpling port was installed below the reactor exit for withdrawing product gas samples for gas chromatographic analyses employing a ⅛ inch diameter, twelve feet long stainless steel column packed with 0.19 weight percent picric acid on carbon black.

Data in Table I show that the presence of water in the 2-butene feed causes increases in butene conversion, and isobutene yield (compare Runs 1 and 2; Runs 4 and 5). The data also show that the presence of water in the butene feed is more effective than the presence of water in the regeneration gas regarding the increase in butene conversion and isobutene yield (compare Runs 1 and 2; Runs 1 and 4).

Especially preferred runs are those with about 1.4–38.0 mole % of water in the butene feed and using wet regeneration gas (Runs 3, 5, 6, 7, 8, 12, 13, 15, 16, 17).

TABLE I

| | Run 1 (Control) | Run 2 (Invention) | Run 3 (Invention) | Run 4 (Control) | Run 5 (Invention) | Run 6 (Invention) | Run 7 (Invention) | Run 8 (Invention) | Run 9 (Invention) |
|---|---|---|---|---|---|---|---|---|---|
| Reactor Temperature (°F.) | 894 | 896 | 893 | 900 | 900 | 900 | 900 | 900 | 899 |
| n-Butene Feed Rate (LHSV) | 2.0 | 2.0 | 2.0 | 2.0 | 2.0 | 2.0 | 2.0 | 2.0 | 2.0 |
| $H_2O$ Content (as mol. % of hydrocarbon feed) | 0 | 3.34 | 3.34 | 0 | 1.67 | 11.4 | 19.5 | 21.1 | 38.8 |
| Regeneration Gas | dry | dry | wet | wet | wet | wet | wet | wet | wet |
| Sampling Time (Hours after start) | 1 | 1 | 1 | 0.5 | 3 | 6.25 | 3.0 | 3.0 | 3.0 |
| Propane in Product (Weight %) | 0.513 | 1.53 | 1.822 | 1.304 | 1.716 | 1.696 | 1.924 | 1.624 | 0.90 |
| Isobutene in Product (Weight %) | 7.513 | 24.44 | 26.295 | 21.097 | 26.85 | 27.721 | 25.12 | 26.127 | 22.2 |
| 1-Butene in Product (Weight %) | 23.40 | 17.3 | 15.98 | 20.642 | 17.17 | 19.12 | 19.02 | 19.411 | 21.9 |
| Trans-2-Butene in Product (Wt. %) | 34.405 | 26.27 | 24.427 | 31.647 | 25.871 | 27.423 | 27.849 | 29.499 | 32.2 |
| Cis-2-Butene in Product (Wt. %) | 28.160 | 20.96 | 19.276 | 21.845 | 20.876 | 20.253 | 22.080 | 20.499 | 22.8 |
| Heavies[a] in Product (Weight %) | 4.82 | 8.71 | 12.432 | 2.712 | 3.779 | 3.223 | 3.341 | 2.318 | — |
| Light Gases[b] in Product (Wt. %) | 0.94 | 0.76 | 2.235 | 0.752 | 0.821 | 0.558 | 0.661 | 0.523 | — |
| Butene Conversion[c] (%) | 14.0 | 35.5 | 40.3 | 25.9 | 36.1 | 33.2 | 31.1 | 30.6 | 25.4 |
| Isobutene Yield[d] (%) | 7.5 | 24.4 | 26.3 | 21.1 | 26.9 | 27.7 | 25.1 | 26.1 | 21.5 |
| Selectivity to Isobutene[e] (%) | 53.7 | 68.8 | 65.3 | 81.5 | 74.4 | 83.5 | 80.7 | 85.3 | 85.0 |

| | Run 10 (Control) | Run 11 (Invention) | Run 12 (Invention) | Run 13 (Invention) | Run 14 (Invention) | Run 15 (Invention) | Run 16 (Invention) | Run 17 (Invention) |
|---|---|---|---|---|---|---|---|---|
| Reactor Temperature (°F.) | 900 | 900 | 900 | 900 | 900 | 900 | 900 | 900 |
| n-Butene Feed Rate (LHSV) | 3.0 | 3.0 | 3.0 | 3.0 | 3.0 | 3.0 | 3.0 | 3.0 |
| $H_2O$ Content (as mol. % of hydrocarbon feed) | 0.03 | 0.33 | 1.67 | 3.34 | 0.33 | 1.67 | 3.34 | 11.4 |
| Regeneration Gas | wet | wet | wet | wet | wet | wet | wet | wet |
| Sampling Time (Hours after start) | 0.5 | 3.0 | 3.0 | 3.0 | 6.0 | 6.3 | 6.4 | 6.5 |
| Propene in Product (Weight %) | 0.559 | 0.825 | 1.316 | 1.452 | 0.681 | 1.197 | 1.348 | 1.411 |
| Isobutene in Product (Weight %) | 13.52 | 18.086 | 25.533 | 26.347 | 15.506 | 23.412 | 25.031 | 25.860 |
| 1-Butene in Product (Weight %) | 20.18 | 22.685 | 20.120 | 19.114 | 23.377 | 20.627 | 20.138 | 19.887 |
| Trans-2-Butene in Product (Wt. %) | 31.49 | 32.175 | 28.855 | 29.726 | 33.582 | 29.653 | 28.793 | 28.546 |
| Cis-2-Butene in Product (Weight %) | 28.54 | 23.737 | 21.335 | 20.225 | 24.728 | 21.909 | 21.299 | 21.204 |
| Heavies[a] in Product (Weight %) | 5.326 | 1.928 | 2.241 | 2.558 | 1.573 | 2.658 | 2.762 | 2.524 |
| Light Gases[b] in Product (Wt. %) | 0.386 | 0.564 | 0.596 | 0.578 | 0.552 | 0.544 | 0.630 | 0.564 |
| Butene Conversion[c] (%) | 19.8 | 21.4 | 29.7 | 30.9 | 18.3 | 27.8 | 29.8 | 30.4 |
| Isobutene Yield[d] (%) | 13.5 | 18.1 | 25.5 | 26.3 | 15.6 | 23.4 | 25.0 | 25.9 |
| Selectivity to Isobutene[e] (%) | 68.2 | 84.6 | 85.9 | 85.1 | 85.2 | 84.2 | 84.0 | 85.2 |

[a] a mixture comprising 1,3-butadiene, 1-pentene, 2-methyl-1-butene, trans- and cis-2-pentene, 2-methyl-2-butene, hexenes.
[b] a mixture comprising $H_2$, $CO_2$, methane, ethane, propane, n-butane, isobutane.
[c] 100 − (weight percent of 1-butene plus weight percent of trans-2-butene plus weight percent of cis-2-butene). Rationale: trans- and cis-2-butene are the components of the feed, and 1-butene is formed by thermal isomerization.
[d] weight percent of isobutene in product.
[e] $\frac{\text{isobutene yield}}{\text{butene conversion}} \times 100$.

EXAMPLE II

The effect of process cycle length (essentially equal to the sampling time) on butene conversion and isobutene yield was investigated. Catalyst, reactor conditions and other pertinent process parameters were essentially the same as those described in Example I.

Data in Table II clearly show that the presence of water in the butene feed causes a significantly greater retention of catalyst activity as indicated by higher butene conversion and isobutene yield than the presence of water in the regeneration gas. After a process duration of about 3 hours, runs with only water in the regeneration gas (Runs 4, 18) showed a dramatic decline in butene conversion and isobutene yield, whereas virtually no changes in these parameters were observed when the feed gas also contained water (Runs 19, 20, 21).

TABLE II

| | Run 4 (Control) | Run 18 (Control) | Run 19 (Invention) | Run 20 (Invention) | Run 21 (Invention) |
|---|---|---|---|---|---|
| Reactor Temperature | 900 | 900 | 900 | 900 | 900 |
| N—Butene Feed Rate (LHSV) | 2.0 | 2.0 | 2.0 | 2.0 | 2.0 |
| $H_2O$ Content (as mol. % of hydrocarbon feed) | 0 | 0 | 21.1 | 21.1 | 21.1 |
| Regeneration Gas | Wet | Wet | Wet | Wet | Wet |
| Sampling Time (Hours) | 0.5 | 3.0 | 1.5 | 3.0 | 6.3 |
| Butene Conversion[a] (%) | 25.9 | 4.6 | 32.0 | 30.6 | 29.4 |
| Isobutene Yield[a] (%) | 21.1 | 4.4 | 27.1 | 26.1 | 25.0 |

[a] definitions in Table I.

EXAMPLE III

In this example, the effect of water in a propylene feed stream on the alumina-catalyzed disproportionation of propylene to ethylene and butenes is described. Reactor and catalyst were the same as described in Example I, except that a pure grade propylene, supplied by Phillips Petroleum Company, Bartlesville, Okla., was used. Operating conditions and product analyses of five representative runs are summarized in Table III.

The data in Table III show that when water is added to the olefin feed, an increase in the formation of 1-butene and isobutene is exhibited (Runs 24, 25, 26) as compared to runs where no water was added to the olefin feed (Runs 22, 23).

TABLE III

|  | Run 22 (Control) | Run 23 (Control) | Run 24 (Invention) | Run 25 (Invention) | Run 26 (Invention) |
| --- | --- | --- | --- | --- | --- |
| Reactor Temperature (°F.) | 900 | 900 | 900 | 900 | 900 |
| Propene Feed Rate (GHSV) | 0.4 | 0.4 | 0.4 | 0.86 | 1.7 |
| $H_2O$ Content (as mol. % of hydrocarbon feed) | 0 | 0 | 3.34 | 3.34 | 3.34 |
| Sampling Time (Hours after start) | 0.5 | 1.0 | 1.0 | 0.5 | 0.5 |
| Propene in Product (Weight %) | 87.291 | 89.831 | 65.04 | 73.302 | 83.239 |
| Isobutene in Product (Weight %) | 3.494 | 2.936 | 8.529 | 6.661 | 4.309 |
| 1-Butene in Product (Weight %) | 0.737 | 0.550 | 3.335 | 2.432 | 1.426 |
| Trans-2-Butene in Product (Wt. %) | 1.200 | 0.858 | 4.514 | 3.319 | 1.854 |
| Cis-2-Butene in Product (Wt. %) | 0.836 | 0.593 | 3.369 | 2.475 | 1.443 |
| Heavies[a] in Product (Weight %) | 4.975 | 3.907 | 10.250 | 8.661 | 6.175 |
| Light Gases[b] in Product (Wt. %) | 1.467 | 1.326 | 4.962 | 3.15 | 1.554 |
| Propene Conversion[c] (%) | 12.7 | 10.2 | 35.0 | 26.7 | 16.8 |
| Isobutene Yield[d] (%) | 3.49 | 2.94 | 8.53 | 6.66 | 4.31 |
| Selectivity to Isobutene[e] (%) | 27.5 | 28.8 | 24.4 | 24.9 | 25.7 |
| Selectivity to Total Butenes[f] (%) | 49.3 | 48.4 | 56.4 | 55.8 | 53.8 |
| Selectivity to Heavies[g] (%) | 39.2 | 38.3 | 29.3 | 32.4 | 36.8 |

[a] a mixture comprising pentenes and higher olefins.
[b] a mixture comprising methane, ethane, ethene, propane, n-butane and isobutane.
[c] 100 − weight percent of propene in product.
[d] weight percent of isobutene in product.
[e]

$$\frac{\text{isobutene yield}}{\text{propene conversion}} \times 100.$$

[f]

$$\frac{\text{Yield of all butenes}}{\text{Propene Conversion}} \times 100.$$

EXAMPLE IV

Data in Table IV show that in the catalytic treatment of 2-butene, essentially in accordance with the procedure of Example I, the disproportionation selectivity to propene and pentenes is about 13–17 weight %. Therefore, even though the skeletal isomerization to isobutene was the primary reaction, the disproportionation reaction occurred to a substantial extent. The fact that the molar ratio of pentenes to propene was approximately 1, especially in the temperature range of 895°–915° F., is a definite indication that pentenes and propene were indeed formed primarily by disproportionation rather than by thermal cracking or other side reactions.

TABLE IV

|  | Run 27 | Run 28 | Run 29 |
| --- | --- | --- | --- |
| Reactor Temp (°F.) | 935° F. | 895° F. | 915° F. |
| Feed Rate (LHSV) | 3.0 | 3.0 | 3.0 |
| Sampling Time (hours) | 2.5–3.0 | 2.75–3.25 | 2.5–3.0 |
| $H_2O$ Content (as mol. % of hydrocarbon feed) | 3.34 | 3.34 | 3.34 |
| Ethane in Product (Weight - %) | 0.047 | 0.076 | 0.062 |
| Propane in Product (Weight - %) | — | — | — |
| Propene in Product (Weight - %) | 2.168 | 1.503 | 1.515 |
| Isobutane in Product (Weight - %) | 0.389 | 0.159 | 0.177 |
| n-Butane in Product (Weight - %) | 0.479 | 0.357 | 0.360 |
| Isobutene in Product (Weight - %) | 31.791 | 25.13 | 26.57 |
| n-Butene in Product (Weight - %) | 18.193 | 19.59 | 19.41 |
| Trans-2-Butene in Product (Weight - %) | 22.816 | 28.410 | 27.391 |
| Cis-2-Butene in Product (Weight - %) | 17.849 | 20.666 | 20.088 |
| Pentenes in Product (Weight - %) | 4.621 | 2.713 | 2.878 |
| Heavies in Product (Weight - %) | 1.644 | 1.368 | 1.550 |
| Butene Conversion (%) | 41.1 | 31.3 | 33.1 |
| Selectivity to Isobutene (%) | 77.4 | 80.2 | 80.3 |
| Selectivity to Propene + Pentenes (%) | 16.5 | 13.5 | 13.3 |
| Moles Pentenes/Moles Propene | 1.28 | 1.08 | 1.14 |

Reasonable variations and modifications are possible from the present invention without departing from the spirit thereof.

We claim:

1. A process for the conversion of at least one olefin which comprises adding to said olefin at least 0.10 mole percent of water and thereafter contacting the resulting wet olefin with an acidic alumina catalyst.

2. A process according to claim 1 wherein said olefin contains from 3 to 16 carbon atoms.

3. A process according to claim 1 wherein water is added to said olefin in an amount from about 0.3 to about 100.0 mole percent.

4. A process according to claim 3 wherein water is added to said olefin in an amount from about 0.3 to about 50.0 mole percent.

5. A process according to claim 1 wherein said olefin is propylene.

6. A process according to claim 1 wherein said olefin is n-butene.

7. A process according to claim 1 wherein said acidic alumina catalyst is either gamma or eta alumina.

8. A process according to claim 1 wherein the temperature is from about 600° F. to about 1200° F.

9. A process according to claim 8 wherein the pressure is from about 0 to about 200 psig.

10. A process according to claim 9 wherein the LHSV is from about 0.1 to about 30 vol./vol./hr.

11. A process for the conversion of at least one olefin which comprises adding to said olefin at least 0.10 mole percent of water and thereafter contacting the resulting wet olefin with an acidic alumina catalyst at a temperature of from about 600° F. to about 1200° F.

12. A process according to claim 11 wherein said olefin contains from 3 to 16 carbon atoms.

13. A process according to claim 11 wherein water is added to said olefin in an amount from about 0.3 to about 100.0 mole percent.

14. A process according to claim 13 wherein water is added to said olefin in an amount from about 0.3 to about 50.0 mole percent.

15. A process according to claim 11 wherein said olefin is propylene.

16. A process according to claim 11 wherein said olefin is n-butene.

17. A process according to claim 11 wherein said acidic alumina catalyst is either gamma or eta alumina.

18. A process according to claim 17 wherein the pressure is from about 0 to about 200 psig.

19. A process according to claim 18 wherein the LHSV is from about 0.1 to about 30 vol./vol./hr.

* * * * *